United States Patent [19]

Pasternak et al.

[11] Patent Number: 4,935,144

[45] Date of Patent: Jun. 19, 1990

[54] CONCENTRATION OF WATER-KETONE COMPOSITIONS

[75] Inventors: Mordechai Pasternak, Spring Valley; Craig R. Bartels; John Reale, Jr., both of Wappingers Falls, all of N.Y.

[73] Assignee: Texaco Inc., White Plains, N.Y.

[21] Appl. No.: 304,691

[22] Filed: Feb. 1, 1989

Related U.S. Application Data

[63] Continuation-in-part of Ser. No. 97,766, Sep. 17, 1987, Pat. No. 4,802,988.

[51] Int. Cl.$^5$ .............................................. E01D 13/00
[52] U.S. Cl. .................................. 210/640; 210/651; 210/654
[58] Field of Search .................. 210/500.42, 640, 651, 210/654

[56] References Cited

U.S. PATENT DOCUMENTS

| | | | |
|---|---|---|---|
| 4,678,555 | 7/1987 | Wernick | 210/500.3 |
| 4,715,960 | 12/1987 | Thompson | 210/500.4 |
| 4,717,480 | 1/1988 | Akedo et al. | 210/638 |
| 4,755,299 | 7/1988 | Brüschke | 210/640 |
| 4,808,313 | 2/1989 | Michizuki et al. | 210/640 |

OTHER PUBLICATIONS

Uragami, Wada, Sugihara, "Studies on Syntheses and Permeabilities of Special Polymer Membranes", Die Angewandte Makromolekulare Chemie 138 (1986), pp. 173-183.

*Primary Examiner*—Frank Sever
*Attorney, Agent, or Firm*—Robert A. Kulason; James J. O'Louglin; Carl G. Seutter

[57] ABSTRACT

Water is separated from methyl isobutyl ketone by pervaporation across a polyvinyl alcohol membrane.

7 Claims, No Drawings

CONCENTRATION OF WATER-KETONE COMPOSITIONS

RELATED APPLICATIONS

This patent application is a continuation-in-part of application Ser. No. 07/97,766 filed Sept. 17, 1987.

Application Ser. No. 07/214,987 filed July 5, 1988, of Mordechai Pasternak, Craig R. Bartels, and John Reale Jr. is directed to the separation of water from a hydrocarbon mixture with an organic oxygenate by the use of membrane technology.

Application Ser. No. 07/97,766 filed Sept. 17, 1987 of John Reale, Jr. and Craig R. Bartels is directed to separation of water from a glycol by the use of membrane technology, now U.S. Pat. No. 4,802,988, Feb. 7, 1988.

Application Ser. No. 07/279,398 filed Nov. 28, 1988 of Craig R. Bartels and John Reale, Jr. is directed to separation of water from organic oxygenates such as isopropanol by the use of membrane technology.

FIELD OF THE INVENTION

This invention relates to the concentration of compositions containing water and a ketone such as methyl isobutyl ketone. More particularly it relates to a membrane technique for effecting separation of water from an aqueous charge mixture containing methyl isobutyl ketone.

BACKGROUND OF THE INVENTION

As well known to those skilled in the art, it is possible to remove water from mixtures thereof with organic liquids by various techniques including adsorption or distillation These conventional processes, particularly distillation, are however, characterized by high capital cost. In the case of distillation for example, the process requires expensive distillation towers, heaters, heat exchangers (reboilers, condensers, etc.), together with a substantial amount of auxiliary equipment typified by pumps, collection vessels, vacuum generating equipment, etc.

Such operations are characterized by high operating costs principally costs of heating and cooling—plus pumping, etc.

Furthermore the properties of the materials being separated, as is evidenced by the distillation curves, may be such that a large number of plates may be required, etc. When the material forms an azeotrope with water, additional problems may be present which for example, may require that separation be effected in a series of steps (e.g. as in two towers) or by addition of extraneous materials to the system.

There are also comparable problems which are unique to adsorption systems.

It has been found to be possible to utilize membrane systems to separate mixtures of miscible liquids by pervaporation. In this process, the charge liquid is brought into contact with a membrane film; and one component of the charge liquid preferentially permeates the membrane. The permeate is then removed as a vapor from the downstream side of the film—typically by sweeping with a carrier gas or by reducing the pressure below the vapor pressure of the permeating species.

Illustrative membranes which have been employed in prior art techniques include those set forth in the following table:

TABLE

| Separating Layer | References |
| --- | --- |
| Nafion brand of perfluorosulfonic acid | Cabasso and Liu J. Memb. Sci. 24, 101 (1985) |
| Sulfonated polyalkene | U.S. Pat. No. 4,728,429 to Cabasso et al |
| Sulfonated polyethylene | Cabasso, Korngold & Liu J. Pol. Sc: Letters, 23, 57 (1985) |
| Fluorinated polyether or Carboxylic Acid fluorides | U.S. Pat. No. 4,526,948 to Dupont as assignee of Resnickto |
| Selemion AMV brand of Asahi Glass cross-linked styrene butadiene (with quaternary ammonium residues on a poylvinyl chloride backing) | Wentzlaff Boddeker & Hattanbach J. Memb. Sci. 22,333 (1985) |
| Cellulose triacetate | Wentzlaff, Boddeker & Hattanback, J. Memb. Sci. 22,333 (1985) |
| Polyacrylonitrile | Neel, Aptel & Clement Desalination 53,297 (1985) |
| Crosslinked Polyvinyl Alcohol | Eur. Patent 0 096 339 to GFT as assignee of Bruschke |
| Poly(maleimide-acrylonitrile) | Yoshikawa et al J. Pol. Sci. 22,2159 (1984) |
| Dextrine - isophorodiisocyanate | Chem. Econ. Eng. Rev., 17, 34 (1985) |

The cost effectiveness of a membrane is determined by the selectivity and productivity. Of the membranes commercially available, an illustrative membrane of high performance is that disclosed in European patent No. 0 096 339 A2 of GFT as assignee of Bruschke—published Dec. 21, 1983.

European Patent No. 0 096 339 A2 to GFT as assignee of Bruschke discloses, as cross-linking agents, diacids (typified by maleic acid or fumaric acid); dihalogen compounds (typified by dichloroacetone or 1,3-dichloroisopropanol); aldehydes, including dialdehydes, typified by formaldehyde. These membranes are said to be particularly effective for dehydration of aqueous solutions of ethanol or isopropanol.

This reference discloses separation of water from alcohols, ethers, ketones, aldehydes, or acids by use of composite membranes. Specifically the composite includes (i) a backing typically about 120 microns in thickness, on which is positioned (ii) a microporous support layer of a polysulfone or a polyacrylonitrile of about 50 microns thickness, on which is positioned (iii) a separating layer of cross-linked polyvinyl alcohol about 2 microns in thickness.

Polyvinyl alcohol may be cross-linked by use of difunctional agents which react with the hydroxyl group of the polyvinyl alcohol. Typical cross-linking agent may include dialdehydes (which yield acetal linkages), diacids or diacid halides (which yield ester linkages), dihalogen compounds or epichlorhydrin (which yield ether linkages) olefinic aldehydes (which yield ether/acetal linkages), boric acid (which yields boric ester linkages), sulfonamidoaldehydes, etc.

See also J. G. Prichard, *Polyvinyl Alcohol, Basic Properties and Uses*, Gordon and Breach Science Publishers, New York (1970) or C. A. Finch, *Polyvinyl Alcohol, Properties and Applications*, John Wiley and Sons, New York (1973).

U.S. Pat. No. 4,728,429 to Cabasso et al, U.S. Pat. No. 4,067,805 to Chiang et al, U.S. Pat. No. 4,526,948 to Resnick, U.S. Pat. No. 3,750,735 to Chiang et al, and U.S. Pat. No. 4,690,766 to Linder et al provide additional background.

It is an object of this invention to provide a novel composite membrane characterized by its ability to effect separation of water from ketones such as methyl isobutyl ketone. Other objects will be apparent to those skilled in the art.

STATEMENT OF THE INVENTION

In accordance with certain of its aspects, this invention is directed to a method of concentrating an aqueous charge composition containing a ketone which comprises maintaining a non-porous separating layer of cast polyvinyl alcohol which has been cross-linked with an aliphatic polyaldehyde containing at least three carbon atoms including those in said aldehyde groups;

maintaining a pressure drop across said non-porous separating layer of polyvinyl alcohol;

passing an aqueous charge composition containing water and ketone into contact with the high pressure side of said non-porous separating layer of polyvinyl alcohol whereby at least a portion of said water in said aqueous charge composition and a lesser portion of ketone in said aqueous charge composition pass by pervaporation through said non-porous separating layer of polyvinyl alcohol as a lean mixture containing more water and less ketone than are present in said aqueous charge composition and said aqueous charge composition is converted to a rich liquid containing less water and more ketone than are present in said aqueous charge composition;

recovering from the low pressure side of said non-porous separating layer of polyvinyl alcohol, said lean mixture containing more water and less ketone than are present in said aqueous charge composition, said lean mixture being recovered in vapor phase at a pressure below the vapor pressure thereof; and recovering from the high pressure side of said non-porous separating layer said rich liquid containing a lower water content and a higher ketone content than are present in said aqueous charge composition.

DESCRIPTION OF THE INVENTION

The composite structure of this invention includes a multi-layer assembly which in the preferred embodiment preferably includes a porous carrier layer which provides mechanical strength and support to the assembly.

THE CARRIER LAYER

This carrier layer, when used, is characterized by its high degree of porosity and mechanical strength. It may be fibrous or non-fibrous, woven or non-woven. In the preferred embodiment, the carrier layer may be a porous, flexible, non-woven fibrous polyester.

A preferred non-woven polyester carrier layer may be formulated of non-woven, thermally-bonded strands and characterized by a fabric weight of 80±8 grams per square yard, a thickness of 4.2±0.5 mils, a tensile strength (in the machine direction) of 31 psi and (in cross direction) of 10 psi, and a Frazier air permeability of 6 cuft/min/sq. ft. @ 0.5 inches of water.

THE POROUS SUPPORT LAYER

The porous support layer of this invention may be formed of a sheet of polymer membrane which is essentially inert with respect to (e.g. insoluble in) the ketone which is used in practice of the process of this invention. The porous support layer may preferably be a membrane of polyacrylonitrile polymer. Typically the polyacrylonitrile may be of thickness of 40–80 microns, say 50 microns. The polyacrylonitrile is preferably characterized by a molecular weight cut-off of about 20,000–40,000.

The acrylonitrile polymers which may be employed may include those having repeating units of the formula:

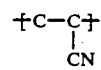

THE SEPARATING LAYER

The separating layer which permits attainment of the separation in accordance with this invention includes a non-porous film of cross-linked polyvinyl alcohol of thickness of about 1–10 microns preferably 1–5 microns, say 3 microns. The layer is formed from polyvinyl alcohol which has been prepared by hydrolysis of polyvinyl acetate-typically 50–100% hydrolyzed, preferably 90–100%, say 100% hydrolyzed. The charge polyvinyl alcohol has a molecular weight of 20,000–200,000 say 115,000. Typically it may be employed as a 5–10 w %, say 7 w % aqueous solution. A commercially available product which may be employed as a 7 w % aqueous solution is the Aldrich brand of 100% hydrolyzed polyvinyl alcohol of molecular weight of about 115,000.

It is a feature of this invention that the membrane or sheet of cross-linked polyvinyl alcohol separating layer is formed in situ on the porous support layer. This is effected by use, as a cross-linking agent, of an aliphatic dialdehyde containing at least three carbon atoms including those in the aldehyde groups. Preferably the aliphatic dialdehyde may contain 3–8, commonly 3–6, carbon atoms, most preferably 5 carbon atoms. Typical alphatic dialdehydes which may be employed may include:

TABLE glutaraldehyde
2-hydroxyhexanedial - 1,6
malonic dialdehyde
succinic dialdehyde
hexanedial - 1,6

The preferred aliphatic dialdehyde is glutaraldehyde. Aldehydes falling outside the scope of this invention typified by formaldehyde, glyoxal, or succinic semialdehyde yield membranes which are characterized by unsatisfactory performance. Performance is judged by the ability of a membrane system to give a permeate containing decreased content of organic oxygenate (from a charge containing a higher content of organic oxygenate and water) with a good flux (kilograms/-meter$^2$-/hour (kmh)) at a predetermined feed temperature and with a vacuum on the permeate side and a condenser cooled by liquid nitrogen. Compositions falling outside the scope of this invention may be characterized by unsatisfactory separation or unsatisfactory productivity (flux) or both.

In situ cross-linking may be carried out by casting 5–10 w %, say 7 w % aqueous solution of polyvinyl alcohol which contains the aliphatic dialdehyde cross-linking agent. The mole ratio of cross-linking agent to polyvinyl alcohol may be 0.05–0.30, say 0.2.

Cross-linking is carried out, in the presence of acid catalyst, preferably inorganic acid. Sulfuric acid is preferred. Hydrochloric acid is much less preferred—because it yields membranes of poor separation, although the flux may be high.

It may be possible in a preferred embodiment to cross-link the polyvinyl alcohol separating layer in one step by adding to the aqueous solution of polyvinyl alcohol and dialdehyde, the acid catalyst, preferably sulfuric acid, in mole ratio of acid to dialdehyde of 0.08–0.14, say 0.1.

The composite membrane may then be cured in an oven at 100° C.–200° C., say 150° C. for 1–30 minutes, say 10 minutes to yield a polyvinyl alcohol film having a thickness of 1–10 microns, say 3 microns.

THE COMPOSITE MEMBRANE

It is a feature of this invention that the composite membrane of this invention may comprise (i) an optional carrier layer, characterized by porosity and mechanical strength, for supporting a porous support layer and a separating layer, (ii) a polyacrylonitrile porous support layer of molecular weight cut off of 20,000–40,000 and (iii) as a non-porous separating layer polyvinyl alcohol of molecular weight of 20,000–200,000 which has been cross-linked with an aliphatic dialdehyde containing 3–9 carbon atoms.

The composite membranes of this invention may be utilized in various configurations. It is, for example, preferable utilize the composite in a plate-and-frame configuration in which separating layers may be mounted on the porous support layer with the carrier layer.

It is also possible to utilize a spiral wound module which includes a non-porous separating layer membrane mounted on a porous support layer and a carrier layer, the assembly being typically folded and bonded or sealed along all the edges but an open edge—to form a bag-like unit which preferably has the separating layer on the outside. A cloth spacer, serving as the permeate or discharge channel is placed within the bag-like unit. The discharge channel projects from the open end of the unit.

There then placed on one face of the bag-like unit, adjacent to the separating layer, and coterminous therewith, a feed channel sheet—typically formed of a plastic net.

The so-formed assembly is wrapped around a preferably cylindrical conduit which bears a plurality of perforations in the wall—preferably in a linear array which is as long as the width of the bag-like unit. The projecting portion of the discharge channel of the bag-like unit is placed over the performations of the conduit; and the bag-like unit is wrapped around the conduit to form a spiral wound configuration.

It will be apparent that, although only one feed channel is present, the single feed channel in the wound assembly will be adjacent to two faces of the membrane layer. The spiral wound configuration may be formed by wrapping the assembly around the conduit a plurality of times to form a readily handleable unit. The unit is fitted within a shell (in manner comparable to a shell-and-tube heat exchanger) provided with an inlet at one end and an outlet at the other. A baffle-like seal between the inner surface of the shell and the outer surface of the spiral-wound input prevents fluid from bypassing the operative membrane system and insures that fluid enters the system principally at one end. The permeate passes from the feed channel, into contact with the separating layer and thence therethrough, into the permeate channel and thence therealong to and through the perforations in the conduit through which it is withdrawn as net permeate.

In use of the spiral wound membrane, charge liquid is permitted to pass through the plastic net which serves as a feed channel and thence into contact with the non-porous separating membranes. The liquid which does not pass through the membranes is withdrawn as retentate. The liquid or vapor which permeates the membrane passes into the volume occupied by the permeate spacer and through this permeate channel to the perforations in the cylindrical conduit through which it is withdrawn from the system. In this embodiment, it will be apparent that the system may not include a carrier layer.

In another embodiment, it is possible to utilize the system of this invention as a tubular or hollow fiber. In this embodiment, the polyacrylonitrile porous support layer may be extruded as a fine tube with a wall thickness of typically 0.001–0.1 mm. The extruded tubes are passed through a bath of polyvinyl alcohol which is cross-linked and cured in situ. A bundle of these tubes is secured (with an epoxy adhesive) at each end in a header; and the fibers are cut so that they are flush with the ends of the header. This tube bundle is mounted within a shell in a typical shell-and-tube assembly.

In operation, the charge liquid is admitted to the tube side and passes through the inside of the tubes and exits as retentate. During passage through the tubes, permeate passes through the non-porous separating layer and permeate is collected in the shell side.

In this embodiment, it will be apparent that the system may not normally include a carrier layer. In still another embodiment, the porous support layer may be omitted; and the separating layer is extruded and thereafter crosslinked and cured in situ prior to mounting in the headers.

PERVAPORATION

It is a feature of the non-porous polyvinyl alcohol separating layer that it is found to be particularly effective when used in a pervaporation process. In pervaporation, a charge liquid containing a more permeable and a less permeable component is maintained in contact with a non-porous separating layer; and a pressure drop is maintained across that layer. The charge liquid dissolves into the membrane and diffuses therethrough. The permeate which passes through the membrane and exits as a vapor may be recovered by condensing at low temperature or alternatively may be swept away by use of a moving stream of gas. Preferably, the permeate side of the membrane is maintained at a low pressure, typically 5 mm. Hg.

For general background on pervaporation, note U.S. Pat. Nos. 4,277,344; 4,039,440; 3,926,798; 3,950,247; 4,035,291; etc.

It is a feature of the process of this invention that the novel membrane may be particularly useful in pervaporation processes for concentrating a charge composition containing water and a ketone. It may be possible to utilize the process of this invention to remove water from immiscible mixtures therewith as in the case of methyl isobutyl ketone (solubility in water at 20° C. of 2.04 parts per 100 parts of water). Water dissolves in methyl isobutyl ketone to the extent of 2.41 parts per 100 parts of water at 20° C. It will be apparent to those skilled in the art that it may be desirable to separate large quantities of water from partially miscible systems as by decantation prior to utilizing the process of the invention to remove the last traces of water.

The advantages of the instant invention are more apparent when the charge liquid is a single phase homogeneous aqueous solution as is the case for example with solutions of methyl isobutyl ketone (MIBK) which at 20°0 C. contain less than about 2 w % water. It is also a feature of this invention that it may be particularly useful to separate azeotropes.

The charge organic ketones which may be treated by the process of this invention may include aliphatic or aromatic ketones. It will be apparent to those skilled in the art that the charge organic ketone used should be inert with respect to the separating membrane. Clearly a system wherein the membrane is attacked by the components of the charge liquid will not yield significant separation for any reasonable period of time.

Illustrative ketones which may be present in aqueous composition which may be treated by the process of this invention may include the following, the first listed being preferred:

TABLE

| methyl isobutyl ketone |
| methyl ethyl ketone |
| acetone |
| pentanone-2 |
| pentanone-3 |

It is believed that the advantages of this invention are most apparent where the ketone is a liquid in which water is soluble—typified by methyl isobutyl ketone.

A typical charge may be an aqueous solution containing 0.5–3.5 say 2.6 w % methyl isobutyl ketone.

In practice of the pervaporation process of this invention, the charge aqueous ketone composition typically at 40° C.–90° C., say 65° C. may be passed into contact with the non-porous separating layer of the membrane of this invention. A pressure drop of about one atmosphere is commonly maintained across the membrane. Typically, the feed or charge side of the membrane is at about atmospheric pressure and the permeate or discharge side of the membrane is at a pressure of about 2–50 preferably 5–20, say 5 mm. Hg.

The permeate which passes through the membrane includes water and a small proportion of the organic ketone from the charge liquid. Typically, the permeate contains 96–99.9, say 99 w % water. Permeate is recovered in vapor phase.

Pervaporation may typically be carried out at a flux of 0.02–0.39, say 0.3 kilograms per square meter per hour (kmh). Typically, the units may show good separation (measured in terms of w % ketone in the permeate during pervaporation of an aqueous solution of ketone through a polyvinyl alcohol separating layer).

The Separation Factor S or Sep which represents the ability of the membrane to separate water is calculated as follows:

$$S = \frac{\left(\frac{X_n}{X_m}\right)_p}{\left(\frac{X_n}{X_m}\right)_f}$$

wherin $X_n$ and $X_m$ are the weight fractions of water and non-aqueous components respectively in the permeate (P) and the feed (F). A system showing no separation at all would have a Separation Factor of 1; and a system showing perfect 100% separation would have a Separation Factor of infinity. The process of the instant invention may have a Separation Factor of as high as 70,000, typically several hundred up to 70,000, say about 62,000. Satisfactory operation may require a Separation Factor of at least about 1000 (this may vary substantially) although good commercial practice may require Separation Factors which are higher. The process of this invention typically yields Separation Factors which are satisfactory.

Practice of the process of this invention will be apparent to those skilled in the art from inspection of the following examples wherein, as elsewhere in this specification, all parts are parts by weight unless otherwise stated. An asterisk indicates a control example.

DESCRIPTION OF SPECIFIC EMBODIMENTS

EXAMPLE I

In this example, which represents the best mode presently known of carrying out the process of this invention, the selective separating layer is mounted on the porous support layer of a commercially available (from Daicel Chemical Industries, LTD) composite containing a non-woven polyester backing as carrier layer, bearing as porous support layer, a microporous polyacrylonitrile ultrafiltration (DUY-L) membrane layer of molecular weight cut-off of 40,000.

The separating layer is formed by applying a 7 w % aqueous solution of polyvinyl alcohol (m.w. 96,000) containing glutaraldehyde (mole ratio of glutaraldehyde to polyvinyl alcohol of 0.2) and sulfuric acid (mole ratio of sulfuric acid to glutaraldehyde of 0.1) to the polyacrylonitrile membrane layer to form a 1.5 mil film. The composite is heated to 150° C. for 10 minutes.

The membrane made by this method is evaluated in a pervaporation cell to which the charge is admitted at 65° C. Permeate pressure is 5 torr at liquid nitrogen temperature.

In this preferred embodiment, the charge solution contains 2.6 w % water and 97.4 w % methyl isobutyl ketone (MIBK). The permeate condenser contains an aqueous solution containing only 0.06 w % MIBK. The Flux (kmh) is 0.29. The Separation Factor is 62,399.

EXAMPLE II

In this Example, the procedure of Example I is carried out, except that the membrane is cured at 125 C. for 15 minutes. The permeate condenser contains only 0.2 w % MIBK. The Flux is 0.39 (kmh). The Separation Factor is 18,693.

The results attained in Example I-II are tabulated infra:

EXAMPLE III-IV

In Example III, the membrane used is the same as that of Example I. In Example IV, the membrane used is the same as that of Example II. The charge at 65° C. is an aqueous solution containing 1.79 w % water and 98.21 w % MIBK.

The procedure of Examples I-II is followed:

TABLE

| Example | Feed Conc w % Water | Feed Conc % MIBK | Separation Factor | Permeate Conc % MIBK | Permeate Conc % Water | Flux kmh |
|---|---|---|---|---|---|---|
| I | 2.6 | 97.4 | 62,399 | 0.06 | 99.94 | 0.29 |
| II | 2.6 | 97.4 | 18,693 | 0.2 | 99.8 | 0.39 |
| III | 1.79 | 98.21 | 30,426 | 0.18 | 99.82 | 0.23 |
| IV | 1.79 | 98.21 | 13,008 | 0.42 | 99.58 | 0.27 |

From the above table, it is apparent that the process of this invention permits attainment of effective separation of water from a charge containing 1.79 w %-2.6 w % water to yield a permeate which is essentially pure water (containing only as little as 0.06 w % MIBK) and a retentate which is MIBK of decreased water content.

EXAMPLES V-XVI*

In Examples V, VIII, XI, and XIV, the membrane employed is the same membrane used in Example II. In Examples VI, IX, XII, and XV, the membrane employed is the same membrane used in Example I. In Control Examples VII*, X*, XIII*, and XVI* the membrane employed is the commercially available GFT 1151 membrane of Geselleschaft fur Trenntechnik—a cross-linked polyvinyl alcohol membrane In this series of Examples, pervaporation is carried out at 60° C.

Pervaporation is carried out, as in Example I (at 60° C.) of charge compositions containing methyl ethyl ketone (MEK) and water.

TABLE

| Example | Feed % Water | Permeate % Water | Separation Factor | Flux kmh |
|---|---|---|---|---|
| V | 2.35 | 98.57 | 2864 | 0.37 |
| VI | 2.35 | 98.65 | 3036 | 0.27 |
| VII* | 2.35 | 99.86 | 29,639 | 0.13 |
| VIII | 1.74 | 99.03 | 5765 | 0.27 |
| IX | 1.74 | 98.84 | 4812 | 0.21 |
| X* | 1.74 | 99.87 | 43,383 | 0.06 |
| XI | 0.75 | 86.11 | 820 | 0.15 |
| XII | 0.75 | 88.25 | 994 | 0.12 |
| XIII* | 0.75 | 11.06 | 16 | 0.04 |
| XIV | 0.39 | 84.93 | 1439 | 0.07 |
| XV | 0.39 | 87.24 | 1746 | 0.05 |
| XVI* | 0.39 | 7.73 | 21 | 0.02 |

From these examples, it is apparent that it is possible to charge an aqueous solution of a ketone to the membrane system of this invention and to attain a permeate which is essentially pure water and a retentate of increased concentration of ketone. For example, it is possible to treat an MEK charge containing small quantities of water to yield permeate containing decreased quantities of MEK under conditions of operation characterized by high Separation Factor and Flux.

EXAMPLES XVII-XVIII-XIX*

In this series of Examples pervaporation a 50° C. is carried out using in Example XVII the membrane of Example I, in Example XVIII the membrane of Example II, and in Control Example XIX* the membrane of Example VII*. Charge is acetone containing 2.01 w % water.

TABLE

| Example | Permeate % Water | Separation Factor | Flux kmh |
|---|---|---|---|
| XVII | 73.01 | 132 | 0.11 |
| XVIII | 75.16 | 148 | 0.15 |
| XIX* | 10.91 | 6 | 0.04 |

From the above Table, it is apparent that practice of the process of this invention permits attainment of a permeate in which the water is concentrated and retentate in which the acetone is concentrated—at a Separation Factor and Flux which are much higher than those of Control Example XIX*.

Results comparable to those attained in Example I may be attained if the ketone is:

TABLE

| Example | Ketone |
|---|---|
| XX | hexanone-2 |
| XXI | pentanone-2 |
| XXII | pentanone-3 |

Although this invention has been illustrated by reference to specific embodiments, it will be apparent to those skilled in the art that various charges and modifications may be made which clearly fall within the scope of the invention.

We claim:

1. The method of concentrating an aqueous composition containing a ketone which comprises maintaining a non-porous separating layer consisting of cast polyvinyl alcohol which has been cross-linked with an aliphatic polyaldehyde containing at least three carbon atoms including those in said aldehyde groups, said layer having a separation factor of up to about 70,000;

maintaining a pressure drop across said non-porous separating layer of polyvinyl alcohol;

passing an aqueous charge composition containing water and ketone into contact with the high pressure side of said non-porous separating layer of polyvinyl alcohol whereby at least a portion of said water in said aqueous charge composition and a lesser portion of ketone in said aqueous charge composition pass by pervaporation through said non-porous separating layer of polyvinyl alcohol as a lean mixture containing more water and less ketone than are present in said aqueous charge composition and said charge composition is converted to a rich liquid containing less water and more ketone than are present in said aqueous charge composition;

recovering from the low pressure side of said non-porous separating layer of polyvinyl alcohol, said lean mixture containing more water and less ketone than are present in said aqueous charge composition, said lean mixture being recovered in vapor phase at a pressure below the vapor pressure thereof; and recovering from the high pressure side of said non-porous separating layer said rich liquid containing a lower water content and a higher ketone content than are present in said aqueous charge composition.

2. The method claimed in claim 1 wherein said aliphatic polyaldehyde is a $C_3$–$C_8$ aliphatic dialdehyde.

3. The method claimed in claim 1 wherein said charge composition contains methyl isobutyl ketone, methyl ethyl ketone, acetone, pentanone-2, pentanone-3, or hexanone-2.

4. The method claimed in claim 1 wherein said charge composition contains methyl isobutyl ketone.

5. The method claimed in claim 1 wherein said charge composition contains a ketone in which water is soluble.

6. The method claimed in claim 1 wherein said charge composition is an aqueous solution of a water-soluble ketone.

7. The method of concentrating an aqueous composition containing a methyl isobutyl ketone which comprises maintaining a non-porous separating layer consisting of cast polyvinyl alcohol which has been cross-linked with glutaraldehyde, said layer having a separation factor of up to about 70,000;

maintaining a pressure drop across said non-porous separating layer of cross-linked polyvinyl alcohol;

passing an aqueous charge composition containing water and methyl isobutyl ketone into contact with the high pressure side of said non-porous separating layer of polyvinyl alcohol whereby at least a portion of said water in said aqueous charge composition and a lesser portion of methyl isobutyl ketone in said aqueous charge composition pass by pervaporation through said non-porous separating layer of polyvinyl alcohol as a lean mixture containing more water and less methyl isobutyl ketone than are present in said aqueous charge composition and said aqueous charge composition is converted to a rich liquid containing less water and more methyl isobutyl ketone than are present in said aqueous charge composition;

recovering from the low pressure side of said non-porous separating layer of polyvinyl alcohol, said lean mixture containing more water and less methyl isobutyl ketone than are present in said aqueous charge composition, said lean mixture being recovered in vapor phase at a pressure below the vapor pressure thereof; and recovering form the high pressure side of said non-porous separating layer said rich liquid containing a lower water content and a higher methyl isobutyl ketone content than are present in said aqueous charge composition.

* * * * *

UNITED STATES PATENT AND TRADEMARK OFFICE
CERTIFICATE OF CORRECTION

PATENT NO.  : 4,935,144
DATED       : June 19, 1990
INVENTOR(S) : Mordechai Pasternak, et al.

It is certified that error appears in the above-identified patent and that said Letters Patent is hereby corrected as shown below:

Col. 2 line 31, correct the spelling of "isophoronediisocyanate";

Col. 7 line 42, after "2.6w%", insert --water and the remainder--;

Col. 9 line 65, cancel "a", insert --at--.

Signed and Sealed this

Tenth Day of September, 1991

Attest:

HARRY F. MANBECK, JR.

Attesting Officer

Commissioner of Patents and Trademarks